(12) United States Patent
Miyanaga et al.

(10) Patent No.: US 10,780,724 B2
(45) Date of Patent: Sep. 22, 2020

(54) HEAT-SENSITIVE RECORDING MATERIAL

(71) Applicant: Nippon Kayaku Kabushiki Kaisha, Chiyoda-ku, Tokyo (JP)

(72) Inventors: Kyohei Miyanaga, Tokyo (JP); Takaaki Kurata, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 241 days.

(21) Appl. No.: 15/781,757

(22) PCT Filed: Dec. 22, 2016

(86) PCT No.: PCT/JP2016/088402
§ 371 (c)(1),
(2) Date: Jun. 6, 2018

(87) PCT Pub. No.: WO2017/111032
PCT Pub. Date: Jun. 29, 2017

(65) Prior Publication Data
US 2018/0345710 A1 Dec. 6, 2018

(30) Foreign Application Priority Data
Dec. 25, 2015 (JP) ................................ 2015-254099

(51) Int. Cl.
*B41M 5/333* (2006.01)
*C07C 309/73* (2006.01)
*B41M 5/155* (2006.01)

(52) U.S. Cl.
CPC .......... *B41M 5/3333* (2013.01); *B41M 5/155* (2013.01); *B41M 5/3335* (2013.01); *C07C 309/73* (2013.01); *B41M 5/3336* (2013.01)

(58) Field of Classification Search
CPC .............. B41M 5/3333; B41M 5/3335; B41M 5/3336; C07C 309/73
See application file for complete search history.

(56) References Cited

U.S. PATENT DOCUMENTS

| 3,539,375 | A | 11/1970 | Baum |
| 6,291,619 | B1 | 9/2001 | Maekawa et al. |
| 9,834,022 | B2 | 12/2017 | Morita |
| 2004/0029056 | A1 | 2/2004 | Tsukada |
| 2005/0255998 | A1 | 11/2005 | Taylor |
| 2015/0284321 | A1 | 10/2015 | Sakai et al. |

FOREIGN PATENT DOCUMENTS

| EP | 1208994 A1 | 5/2002 |
| JP | 57-11088 A | 1/1982 |
| JP | 11-212258 A | 8/1999 |
| JP | 2005-518966 A | 6/2005 |
| JP | 4601174 B2 | 12/2010 |
| JP | 2016-83858 A | 5/2016 |
| WO | 00/35679 A1 | 6/2000 |
| WO | 2014/080615 A1 | 5/2014 |
| WO | 2015/111518 A1 | 7/2015 |

OTHER PUBLICATIONS

Konovalova et al. "Reaction of N-Arylcarbamoyl-1,4-benzoquinone Imines with Sodium Arenesulfiniates", Rus. J. of Org. Chem., 2014, vol. 50, p. 1292-1300. (Year: 2014).*
International Search Report dated Feb. 7, 2017 in corresponding PCT application No. PCT/JP2016/088402.
International Preliminary Report on Patentability dated Jun. 26, 2018 in corresponding PCT application No. PCT/JP2016/088402.
Gwaltney et al., "Novel Sulfonate Derivatives: Potent Antimitotic Agents", Bioorganic & Medicinal Chemistry Letters, vol. 11, Iss. 13, pp. 1671-1673, 2001.
Brazilian communication, with English translation, dated Feb. 11, 2020 in corresponding Brazilian patent application No. BR112018011156-2.
European communication dated Sep. 17, 2019 in corresponding European patent application No. 16878919.6.

* cited by examiner

*Primary Examiner* — Gerard Higgins
(74) *Attorney, Agent, or Firm* — Nields, Lemack & Frame, LLC

(57) ABSTRACT

To provide a heat-sensitive recording material which produces images with excellent resistance to water, while producing background with resistance to heat. A heat-sensitive recording material which is characterized by containing at least one compound represented by general formula (1) as a color-developing compound:

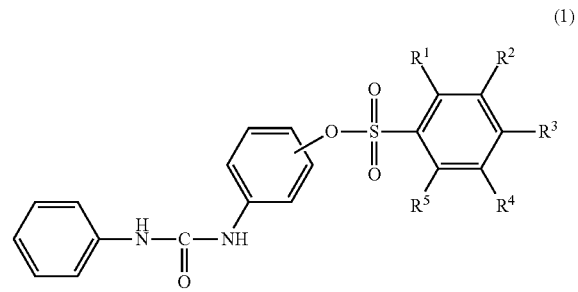

(1)

wherein, R1-R5 each independently represents a hydrogen atom, a halogen atom, a nitro group, an amino group, an alkyl group, an alkoxy group, an aryloxy group, an alkylcarbonyloxy group, an arylcarbonyloxy group, an alkylcarbonylamino group, an arylcarbonylamino group, an alkylsulfonylamino group, an arylsulfonylamino group, a monoalkylamino group, a dialkylamino group or an arylamino group.

12 Claims, No Drawings

HEAT-SENSITIVE RECORDING MATERIAL

TECHNICAL FIELD

The present invention relates to a heat-sensitive recording material which can produce an image with excellent water resistance as well as a background with excellent heat resistance.

BACKGROUND ART

Heat-sensitive recording materials are generally prepared by separately making fine particles of a leuco dye and fine particles of a color-developing compound such as a phenolic compound, mixing these fine particles, and adding thereto additives such as a binder, a sensitizer, a filler and a lubricant. They are then applied to paper, films, synthetic paper or the like. The recording materials effect color development (printing) through chemical reactions that occur by melting one or both of the leuco dye and the color-developing compound by heating, thereby bring the compounds into contact with each other. To induce the color formation of such heat-sensitive recording materials, a thermal printer, comprising a thermal head, or the like is used. Such a thermal recording method, as compared with other recording methods, has been widely used in, for example, the fields of facsimile machines, printers for computers and calculators, recorders for medical instruments, automatic ticket machines and heat-sensitive recording labels and the like, because of its advantages of (1) absence of noise during recording; (2) no requirement to develop or fix an image; (3) freedom from maintenance; (4) a relative inexpensiveness of machines; etc.

In recent years, as the scope of applications of heat-sensitive recording materials has expanded, there has been an increasing need for high-speed recording. Specifically, it has been strongly desired to develop a heat-sensitive recording material capable of enabling high-speed recording by having excellent thermal responsiveness. In general, when thermal responsiveness is enhanced, a color-developing compound having a low melting point and reduced heat of fusion are required. However, such properties tend to cause so-called background fogging, that is, darkening of the unrecorded parts (backgrounds) of heat-sensitive recording materials during manufacture, use, or storage. As a result, a need to improve the stability in backgrounds has arisen.

In general, a color-developing compound having a phenolic hydroxyl group has a high color-developing capability. Among such compounds, bisphenol-based compounds can produce colored images with high intensity, and there are many reports regarding such compounds as 2,2-bis(4-hydroxyphenylpropane) (bisphenol A) (Patent Literature 1), 4,4'-dihydroxydiphenylsulfone (bisphenol S) (Patent Literature 2), and the like. However, they have disadvantages of reduced thermal responsiveness due to their high melting points and of images with reduced water resistance. In addition, it has been pointed out that use of phenol-based compounds such as bisphenol A causes the endocrine problem. Accordingly, a non-phenol-based color-developing compound, which has no phenol structure, has been called for.

In this regard, a heat-sensitive recording material containing N-(p-toluenesulfonyl)-N'-(3-p-toluenesulfonyloxyphenyl)urea or the like as a color-developing compound has been proposed in order to improve background brightness before and after developing color as well as image stability (Patent Literature 3). However, the heat-sensitive recording material described in this literature does not necessarily produce images with sufficient water resistance and background with sufficient heat resistance.

CITATION LIST

Patent Literature

PATENT LITERATURE 1: US-3539375
PATENT LITERATURE 2: JP-A-57-11088
PATENT LITERATURE 3: JP-B-4601174

SUMMARY OF INVENTION

Technical Problem

An object of the present invention is to solve the problems in the above-described state of the art. More specifically, an object of the present invention is to provide a heat-sensitive recording material which produces an image with excellent water resistance and a background with excellent stability to heat.

Solution to Problem

The present inventor has diligently conducted studies to attain the object, and as a result, has newly found that a heat-sensitive recording material comprising a compound having a certain structure as a color-developing compound produce an image with excellent water resistance as well as a background with excellent resistance to heat, and has completed the present invention.

That is, the present invention relates to:

[1] a heat-sensitive recording material comprising at least one compound represented by the general formula (1):

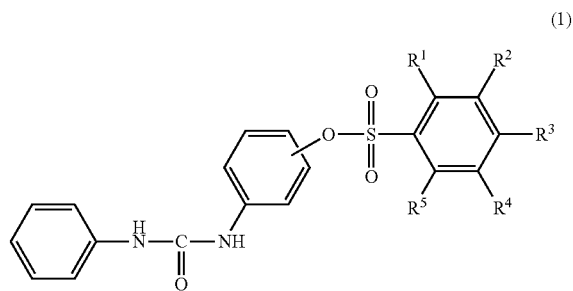

(1)

wherein in the formula (1), $R^1$ to $R^5$ each independently represent a hydrogen atom, a halogen atom, a nitro group, an amino group, an alkyl group, an alkoxy group, an aryloxy group, an alkylcarbonyloxy group, an arylcarbonyloxy group, an alkylcarbonylamino group, an arylcarbonylamino group, an alkylsulfonylamino group, an arylsulfonylamino group, a monoalkylamino group, a dialkylamino group, or an arylamino group;

[2] the heat-sensitive recording material according to [1], wherein the compound of the general formula (1) is a compound represented by the general formula (2):

(2)

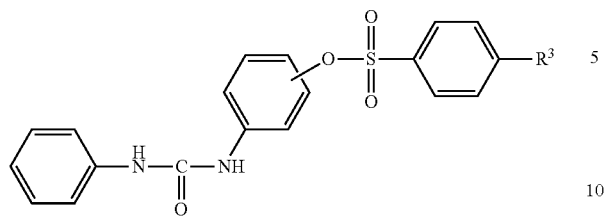

wherein in the formula (2), $R^3$ is as defined above;

[3] the heat-sensitive recording material according to [2], wherein in the general formula (2), $R^3$ is a methyl group;

[4] a heat-sensitive recording layer comprising the heat-sensitive recording material according to any one of [1] to [3];

[5] a heat-sensitive recording paper comprising the heat-sensitive recording layer according to [4];

[6] a compound represented by the general formula (1);

(1)

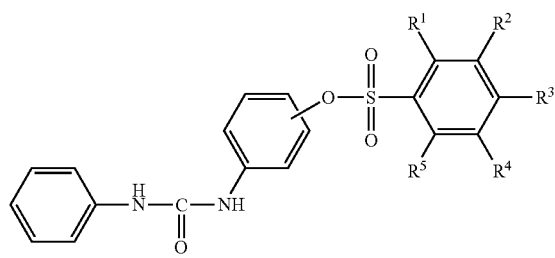

wherein, $R^1$ to $R^5$ each independently represent a hydrogen atom, a halogen atom, a nitro group, an amino group, an alkyl group, an aryloxy group, an alkylcarbonyloxy group, an arylcarbonyloxy group, an alkylcarbonylamino group, an arylcarbonylamino group, an alkylsulfonylamino group, an arylsulfonylamino group, a monoalkylamino group, a dialkylamino group, or an arylamino group;

[7] a compound represented by the general formula (2):

(2)

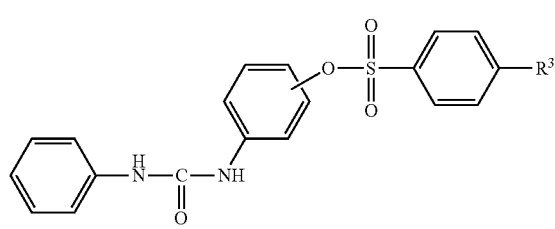

wherein, $R^3$ is as defined above; and

[8] a compound represented by the formulae (3) to (5).

(3)

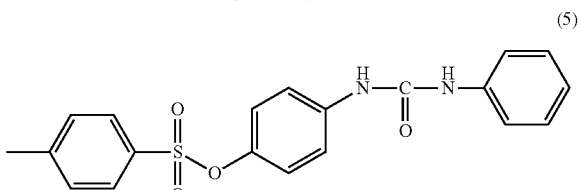

(4)

(5)

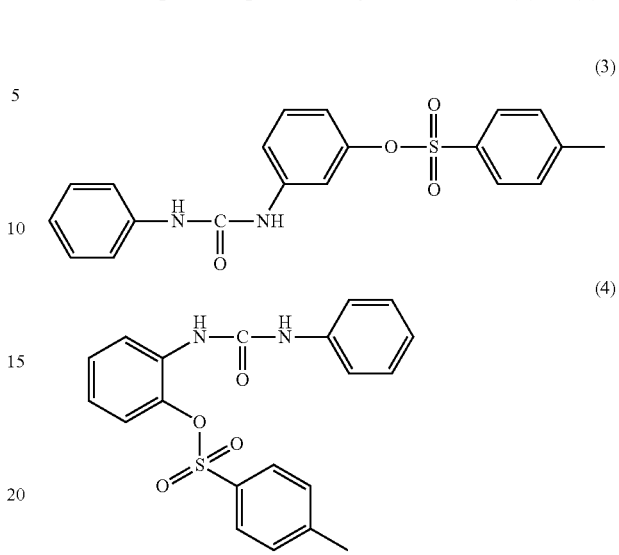

Advantageous Effects of Invention

According to the present invention, provided be can a heat-sensitive recording material which produces an image with excellent resistance to water and a background with high stability to heat.

DESCRIPTION OF EMBODIMENTS

The present invention is described in details by referring to embodiments hereinbelow. It is to be noted that the present invention is not limited by the following embodiments.

As described above, the present invention relates to the above-described compound represented by the general formula (1), as well as a heat-sensitive recording material comprising the same as a color-developing compound, and a heat-sensitive recording layer and a heat-sensitive recording paper comprising the same.

In one embodiment of the present invention, examples of the halogen atom in $R^1$ to $R^5$ of the general formula (1) include a fluorine atom, a chlorine atom, and a bromine atom; and a fluorine atom and a chlorine atom are preferable.

In one embodiment of the present invention, examples of the alkyl group in $R^1$ to $R^5$ of the general formula (1) include a linear, branched, or cyclic alkyl group. Among them, a linear or branched alkyl group is preferable, and a linear alkyl group is more preferable. The number of carbon atoms of the alkyl group is usually C1 to C12, preferably C1 to C8, more preferably C1 to C6, and even more preferably C1 to C4. Specific examples of the alkyl group include a linear alkyl group (preferably a C1 to C6 linear alkyl group) such as methyl, ethyl, n-propyl, n-butyl, n-pentyl, n-hexyl, n-octyl, n-nonyl, n-decyl, n-undecyl, and n-dodecyl; a branched alkyl group (preferably a C3 to C10 branched alkyl group)

such as isopropyl, isobutyl, sec-butyl, t-butyl, isopentyl, isohexyl, and isooctyl; and a cyclic alkyl group (preferably a C3 to C7 cyclic alkyl group) such as cyclopropyl, cyclobutyl, cyclopentyl, cyclohexyl and the like.

In one embodiment of the present invention, examples of the alkoxy group in $R^1$ to $R^5$ of the general formula (1) include a linear, branched, or cyclic alkoxy group. Among them, a linear or branched alkoxy group is preferable, and a linear alkoxy group is more preferable. The number of carbon atoms of the alkoxy group is usually C1 to C12, preferably C2 to C8, more preferably C2 to C6, and even more preferably C2 to C4. Specific examples of the alkoxy group include a linear alkoxy group (preferably a C2 to C6 linear alkoxy group) such as methoxy, ethoxy, n-propoxy, n-butoxy, n-pentoxy, n-hexyloxy, n-heptoxy, n-octyloxy, n-nonyloxy, and n-decyloxy; a branched alkoxy group (preferably a C3 to C10 branched alkoxy group) such as isopropoxy, isobutoxy, sec-butoxy, t-butoxy, isoamyloxy, t-amyloxy, isohexyloxy, t-hexyloxy, isoheptoxy, t-heptoxy, isooctyloxy, t-octyloxy, 2-ethylhexyloxy, isononyloxy, and isodecyloxy; a cyclic alkoxy group (preferably a C3 to C7 cyclic alkoxy group) such as cyclopropoxy, cyclobutoxy, cyclopentoxy, cyclohexyloxy, cycloheptoxy and the like.

In one embodiment of the present invention, examples of the aryloxy group in $R^1$ to $R^5$ of the general formula (1) preferably include a C6 to C12 aryloxy group, and specific examples thereof include phenoxy, naphthyloxy, biphenyloxy and the like.

In one embodiment of the present invention, examples of the alkylcarbonyloxy group in $R^1$ to $R^5$ of the general formula (1) include a linear, branched, or cyclic alkylcarbonyloxy group, and a C1 to C10 alkylcarbonyloxy group is preferable. In addition, a linear or branched alkylcarbonyloxy group is preferable, and a linear alkylcarbonyloxy group is more preferable. Specific examples of the alkylcarbonyloxy group include a linear alkylcarbonyloxy group (preferably a carbonyloxy group having a C1 to C6 linear alkyl group) such as methylcarbonyloxy, ethylcarbonyloxy, n-propylcarbonyloxy, n-butylcarbonyloxy, n-pentylcarbonyloxy, n-hexylcarbonyloxy, n-heptylcarbonyloxy, n-octylcarbonyloxy, n-nonylcarbonyloxy, and n-decylcarbonyloxy; a branched alkylcarbonyloxy group (preferably a carbonyloxy group having a C3 to C10 branched alkyl group) such as isopropylcarbonyloxy, isobutylcarbonyloxy, sec-butylcarbonyloxy, t-butylcarbonyloxy, isoamylcarbonyloxy, t-amylcarbonyloxy, isohexylcarbonyloxy, t-hexylcarbonyloxy, isoheptylcarbonyloxy, t-heptylcarbonyloxy, isooctylcarbonyloxy, t-octylcarbonyloxy, 2-ethylhexylcarbonyloxy, isononylcarbonyloxy, and isodecylcarbonyloxy; and a cyclic alkylcarbonyloxy group (preferably a carbonyloxy group having a C3 to C7 cyclic alkyl group) such as cyclopropylcarbonyloxy, cyclobutylcarbonyloxy, cyclopentylcarbonyloxy, cyclohexylcarbonyloxy, and cycloheptylcarbonyloxy.

In one embodiment of the present invention, examples of the arylcarbonyloxy group in $R^1$ to $R^5$ of the general formula (1) preferably include a C6 to C12 arylcarbonyloxy group, and specific examples thereof include phenylcarbonyloxy, naphthylcarbonyloxy, biphenylcarbonyloxy and the like.

In one embodiment of the present invention, examples of the alkylcarbonylamino group in $R^1$ to $R^5$ of the general formula (1) include a linear, branched, or cyclic alkylcarbonylamino group, and a C1 to C10 alkylcarbonylamino group is preferable. In addition, a linear or branched alkylcarbonylamino group is preferable, and a linear alkylcarbonylamino group is more preferable. Specific examples of the alkylcarbonylamino group include a linear alkylcarbonylamino group (preferably a carbonylamino group having a C1 to C6 linear alkyl group) such as methylcarbonylamino, ethylcarbonylamino, n-propylcarbonylamino, n-butylcarbonylamino, n-pentylcarbonylamino, n-hexylcarbonylamino, n-heptylcarbonylamino, n-octylcarbonylamino, n-nonylcarbonylamino, and n-decylcarbonylamino; a branched alkylcarbonylamino group (preferably a carbonylamino group having a C3 to C10 branched alkyl group) such as isopropylcarbonylamino, isobutylcarbonylamino, sec-butylcarbonylamino, t-butylcarbonylamino, isoamylcarbonylamino, t-amylcarbonylamino, isohexylcarbonylamino, t-hexylcarbonylamino, isoheptylcarbonylamino, t-heptylcarbonylamino, isooctylcarbonylamino, t-octylcarbonylamino, 2-ethylhexylcarbonylamino, isononylcarbonylamino, and isodecylcarbonylamino; and a cyclic alkylcarbonylamino group (preferably a carbonylamino group having a C3 to C7 cyclic alkyl group) such as cyclopropylcarbonylamino, cyclobutylcarbonylamino, cyclopentylcarbonylamino, cyclohexylcarbonylamino, and cycloheptylcarbonylamino.

In one embodiment of the present invention, examples of the arylcarbonylamino group in $R^1$ to $R^5$ of the general formula (1) preferably include a C6 to C12 arylcarbonylamino group, and specific examples thereof include phenylcarbonylamino, naphthylcarbonylamino, biphenylcarbonylamino and the like.

In one embodiment of the present invention, examples of the alkylsulfonylamino group in $R^1$ to $R^5$ of the general formula (1) include a linear, branched, or cyclic alkylsulfonylamino group, and a C1 to C10 alkylsulfonylamino group is preferable. In addition, a linear or branched alkylsulfonylamino group is preferable, and a linear alkylsulfonylamino group is more preferable. Specific examples of the alkylsulfonylamino group include a linear alkylsulfonylamino group (preferably a sulfonylamino group having a C1 to C6 linear alkyl) such as methylsulfonylamino, ethylsulfonylamino, n-propylsulfonylamino, n-butylsulfonylamino, n-pentylsulfonylamino, n-hexylsulfonylamino, n-heptylsulfonylamino, n-octylsulfonylamino, n-nonylsulfonylamino, and n-decylsulfonylamino; a branched alkylsulfonylamino group (preferably a sulfonylamino group having a C3 to C10 branched alkyl group) such as isopropylsulfonylamino, isobutylsulfonylamino, sec-butylsulfonylamino, t-butylsulfonylamino, isoamylsulfonylamino, t-amylsulfonylamino, isohexylsulfonylamino, t-hexylsulfonylamino, isoheptylsulfonylamino, t-heptylsulfonylamino, isooctylsulfonylamino, t-octylsulfonylamino, 2-ethylhexylsulfonylamino, isononylsulfonylamino, and isodecylsulfonylamino; and a cyclic alkylsulfonylamino group (preferably a sulfonylamino group having a C3 to C7 cyclic alkyl group) such as cyclopropylsulfonylamino, cyclobutylsulfonylamino, cyclopentylsulfonylamino, cyclohexylsulfonylamino, and cycloheptylsulfonylamino.

In one embodiment of the present invention, examples of the arylsulfonylamino group in $R^1$ to $R^5$ of the general formula (1) preferably include a C6 to C12 arylsulfonylamino group, and specific examples thereof include phenylsulfonylamino, toluenesulfonylamino, naphthylsulfonylamino, biphenylsulfonylamino and the like.

In one embodiment of the present invention, examples of the monoalkylamino group in $R^1$ to $R^5$ of the general formula (1) include a linear, branched, or cyclic monoalkylamino group, and a mono-C1 to C10 alkylamino group is preferable. In addition, a linear or branched monoalkylamino group is preferable, and a linear monoalkylamino group is more preferable. Specific examples of the monoalkylamino group include a linear monoalkylamino group (preferably a C1 to C6 linear monoalkylamino group) such as methylamino, ethylamino, n-propylamino, n-butylamino, n-pentylamino, n-hexylamino, n-heptylamino, n-octylamino, n-nonylamino, and n-decylamino; a branched monoalkylamino group (preferably a C3 to C10 branched monoalkylamino group) such as isopropylamino, isobutylamino, sec-butylamino, t-butylamino, isoamylamino, t-amylamino, isohexylamino, t-hexylamino, isoheptylamino, t-heptylamino, isooctylamino, t-octylamino, 2-ethylhexylamino, isononylamino, and isodecylamino; and a cyclic monoalkylamino group (preferably a C3 to C7 monocyclic alkylamino group) such as cyclopropylamino, cyclobutylamino, cyclopentylamino, cyclohexylamino, and cycloheptylamino.

In one embodiment of the present invention, examples of the dialkylamino group in $R^1$ to $R^5$ of the general formula (1) include a linear, branched, or cyclic dialkylamino group, and a di-C1 to C10 alkylamino group is preferable. In addition, a linear or branched dialkylamino group is preferable, and a linear dialkylamino group is more preferable. Specific examples of the dialkylamino group include a linear dialkylamino group (preferably a dialkylamino group having two C1 to C6 linear alkyl groups) such as dimethylamino, diethylamino, di-n-propylamino, di-n-butylamino, di-n-pentylamino, di-n-hexylamino, di-n-heptylamino, di-n-octylamino, di-n-nonylamino, and di-n-decylamino; a branched dialkylamino group (preferably a dialkylamino group having two C3 to C10 branched alkyl groups) such as diisopropylamino, diisobutylamino, di-sec-butylamino, di-t-butylamino, diisoamylamino, di-t-amylamino, diisohexylamino, di-t-hexylamino, diisoheptylamino, di-t-heptylamino, diisooctylamino, di-t-octylamino, di-(2-ethylhexyl)amino, diisononylamino, and diisodecylamino; and a cyclic dialkylamino group (preferably a dialkylamino group having two C3 to C7 cyclic alkyl groups) such as dicyclopropylamino, dicyclobutylamino, dicyclopentylamino, dicyclohexylamino, and dicycloheptylamino.

In one embodiment of the present invention, examples of the arylamino group in $R^1$ to $R^5$ of the general formula (1) include a monoarylamino group or a diarylamino group, and a mono-C6 to C12 arylamino group is preferable. Specific examples thereof include phenylamino (anilino), naphthylamino, biphenylamino and the like. In addition, examples of the di-C6 to C12 arylamino group include diphenylamino, dinaphthylamino, di(biphenyl)amino and the like.

According to preferable embodiments of the present invention, $R^1$ to $R^5$ in the above-described general formula (1) are an alkyl group or a hydrogen atom, more preferably a linear C1 to C8 alkyl group or a hydrogen atom, even more preferably a linear C1 to C4 alkyl group or a hydrogen atom, and especially preferably a methyl group or a hydrogen atom.

Alternatively, according to other preferable embodiments of the present invention, $R^1$, $R^2$, $R^4$, and $R^5$ in the above-described general formula (1) are a hydrogen atom, and $R^3$ is a hydrogen atom, a halogen atom, a nitro group, an amino group, an alkyl group, an alkoxy group, an aryloxy group, an alkylcarbonyloxy group, an alkylcarbonylamino group, an arylcarbonylamino group, an alkylsulfonylamino group, an arylsulfonylamino group, a monoalkylamino group, a dialkylamino group, or an arylamino group, preferably a hydrogen atom or an alkyl group, more preferably a hydrogen atom or a C1 to C8 alkyl group (preferably a linear alkyl group), even more preferably a hydrogen atom or a C1 to C4 alkyl group (preferably a linear alkyl group), and especially preferably a methyl group.

A partial skeleton represented by the following general formula (6) which binds to one benzene ring of the diphenylurea structure in the above-described general formula (1) may be at an ortho position, a meta position, or a para position to the aminocarbonyl group on the benzene ring, preferably at an ortho position or a meta position, and especially preferably at a meta position.

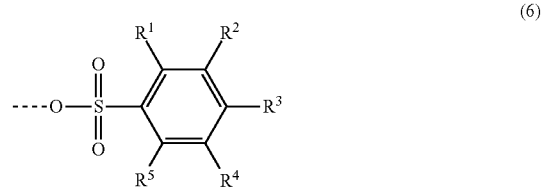

According to preferable embodiments of the present invention, the color-developing compound may be a compound of the above-described general formula (1) in which $R^1$ to $R^5$ are an alkyl group or a hydrogen atom, and a partial skeleton represented by the general formula (6) is at an ortho position or a meta position to the aminocarbonyl group on the benzene ring. More preferably, the color-developing compound may be a compound of the above-described general formula (1) in which $R^1$ to $R^5$ are a linear C1 to C8 alkyl group or a hydrogen atom, and a partial skeleton represented by the general formula (6) is at a meta position to the aminocarbonyl group on the benzene ring. Even more preferably, the color-developing compound is a compound of the above-described general formula (1) in which $R^1$ to $R^5$ are a linear C1 to C4 alkyl group or a hydrogen atom, and a partial skeleton represented by the general formula (6) is at a meta position to the aminocarbonyl group on the benzene ring. Especially preferably, the color-developing compound may be a compound of the above-described general formula (1) in which $R^1$ to $R^5$ are methyl groups or hydrogen atoms, and a partial skeleton represented by the general formula (6) is at a meta position to the aminocarbonyl group on the benzene ring.

Alternatively, according to other preferable embodiments of the present invention, the color-developing compound may be a compound of the above-described general formula (1) in which $R^1$, $R^2$, $R^4$, and $R^5$ are a hydrogen atom, $R^3$ is a hydrogen atom, a halogen atom, a nitro group, an amino group, an alkyl group, an alkoxy group, an aryloxy group, an alkylcarbonyloxy group, an alkylcarbonylamino group, an arylcarbonylamino group, an alkylsulfonylamino group, an arylsulfonylamino group, a monoalkylamino group, a dialkylamino group, or an arylamino group, and a partial skeleton represented by the general formula (6) is at an ortho position, a meta position, or a para position to the aminocarbonyl group on the benzene ring. Preferably, the color-developing compound may be a compound of the above-described general formula (1) in which $R^1$, $R^2$, $R^4$, and $R^5$ are a hydrogen atom, $R^3$ is a hydrogen atom or an alkyl group, and a partial skeleton represented by the general formula (6) is at an ortho position or a meta position to the aminocarbonyl group on the benzene ring. More preferably, the color-developing compound is may be a compound of the above-described general formula (1) in which $R^1$, $R^2$, $R^4$, and $R^5$ are a hydrogen atom, $R^3$ is a linear C1 to C8 alkyl group or a hydrogen atom, and a partial skeleton represented by the general formula (6) is at a meta position to the aminocarbonyl group on the benzene ring. Even more preferably, the color-developing compound may be a compound of the above-described general formula (1) in which $R^1$, $R^2$, $R^4$, and $R^5$ are a hydrogen atom, $R^3$ is a linear C1 to C4 alkyl group or a hydrogen atom, and a partial skeleton represented by the general formula (6) is at a meta position to the aminocarbonyl group on the benzene ring. Especially preferably, the color-developing compound may be a compound of the above-described general formula (1) in which $R^1$, $R^2$, $R^4$, and $R^5$ are hydrogen atoms, $R^3$ is a methyl group, and a partial skeleton represented by the general formula (6) is at a meta position to the aminocarbonyl group on the benzene ring.

Specific examples of the compound according to the present invention include, but are not limited to, compounds described in the following Table 1.

TABLE 1

| Compound No. | Structural formula |
| --- | --- |
| 1 | |
| 2 | |
| 3 | |
| 4 | |
| 5 | |
| 6 | |

TABLE 1-continued

| Compound No. | Structural formula |
|---|---|
| 7 | 2-(3-phenylureido)phenyl 4-chlorobenzenesulfonate |
| 8 | 3-(3-phenylureido)phenyl 4-chlorobenzenesulfonate |
| 9 | 4-(3-phenylureido)phenyl 4-chlorobenzenesulfonate |
| 10 | 2-(3-phenylureido)phenyl 4-nitrobenzenesulfonate |
| 11 | 3-(3-phenylureido)phenyl 4-nitrobenzenesulfonate |
| 12 | 4-(3-phenylureido)phenyl 4-nitrobenzenesulfonate |
| 13 | 2-(3-phenylureido)phenyl 4-aminobenzenesulfonate |

TABLE 1-continued

| Compound No. | Structural formula |
| --- | --- |
| 14 | |
| 15 | |
| 16 | |
| 17 | |
| 18 | |
| 19 | |
| 20 | |

TABLE 1-continued

| Compound No. | Structural formula |
| --- | --- |
| 21 | (structure) |
| 22 | (structure) |
| 23 | (structure) |
| 24 | (structure) |
| 25 | (structure) |
| 26 | (structure) |
| 27 | (structure) |

TABLE 1-continued

| Compound No. | Structural formula |
| --- | --- |
| 28 | |
| 29 | |
| 30 | |
| 31 | |
| 32 | |
| 33 | |
| 34 | |

TABLE 1-continued

| Compound No. | Structural formula |
|---|---|
| 35 | (structure) |
| 36 | (structure) |
| 37 | (structure) |
| 38 | (structure) |
| 39 | (structure) |
| 40 | (structure) |
| 41 | (structure) |

| Compound No. | Structural formula |
|---|---|
| 42 | |
| 43 | |
| 44 | |
| 45 | |

Next, methods for producing compounds of the present invention are described.

Compounds of the present invention are produced by combining two known production processes described below.

[Production Process 1]

A compound of the above-described general formula [1-2] can be produced by reacting the aminophenol of the formula [1-1] with an acid halide of the formula [1-5] or an acid anhydride of the formula [1-6] in the presence or absence of a base.

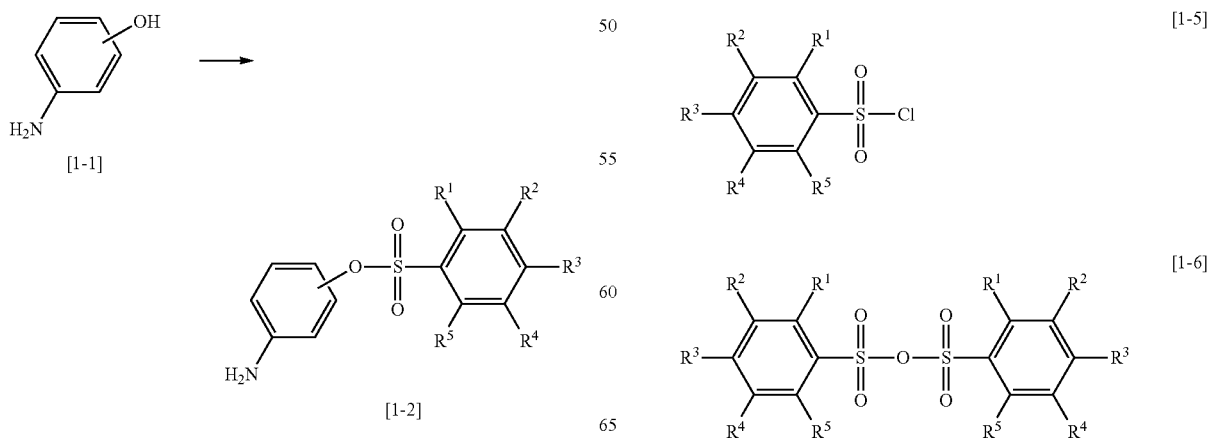

wherein $R^1$ to $R^5$ are as defined above.

The amount of the acid halide or the acid anhydride used in this reaction is 0.1 to 50 molar times, and is preferably 1 to 5 molar times, with respect to 1 mole of the aminophenol of the formula [1-1].

In general, the acid halide can be produced by reacting a compound represented by the following general formula [1-4] with thionyl chloride, oxalyl chloride or the like.

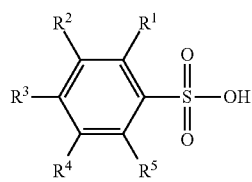

[1-4]

wherein $R^1$ to $R^5$ are as defined above.

In general, the acid anhydride can be produced by reacting a compound represented by the above-described general formula [1-4] with phosphorus pentoxide, dicyclohexylcarbodiimide or the like.

Examples of the base which is used, if desired, in this reaction include: an inorganic base such as sodium hydroxide, potassium hydroxide, sodium bicarbonate, sodium carbonate, potassium bicarbonate, potassium carbonate, and cesium carbonate; and an organic base such as triethylamine, pyridine, and diisopropylethylamine. The amount of the base used may be 0.1 to 50 molar times, and may be preferably 1 to 5 molar times, with respect to 1 mole of the aminophenol of the formula [1-1].

[Production Process 2]

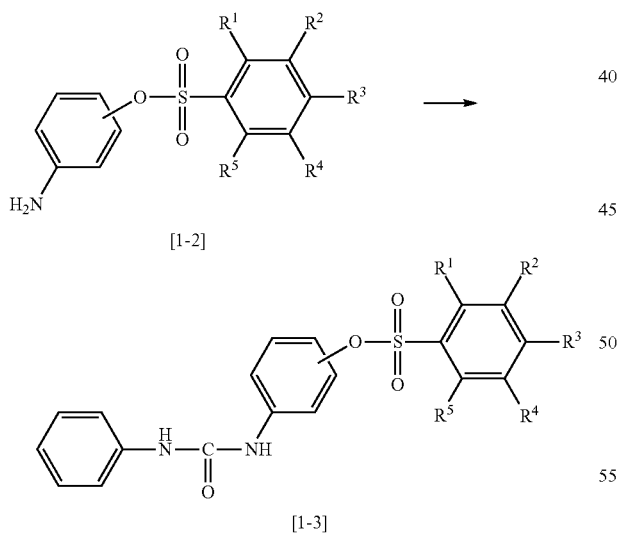

wherein $R^1$ to $R^5$ are as defined above.

A compound of the general formula [1-3] can be produced by reacting a compound of the general formula [1-2] with phenyl isocyanate, in the presence or absence of a base. The amount of phenyl isocyanate used in this reaction is usually 0.1 to 50 molar times, and is preferably 0.1 to 5 molar times, with respect to 1 mole of a compound of the general formula [1-2].

Examples of the base which is used, if desired, in this reaction include: an inorganic base such as sodium hydroxide, potassium hydroxide, sodium bicarbonate, sodium carbonate, potassium bicarbonate, potassium carbonate, and cesium carbonate; and an organic base such as triethylamine and diisopropylethylamine. The amounts of these bases used are 0.1 to 50 molar times, and are preferably 1 to 5 molar times, with respect to 1 mole of the compound of the general formula [1-2].

The solvent for use in these two production processes are not particularly limited as long as the solvent has no influence on these reactions. Examples of the solvent include: an amide compound such as N,N-dimethylformamide, N,N-dimethylacetamide, and N-methylpyrrolidone; a halogenated hydrocarbon compound such as methylene chloride and chloroform; an aromatic hydrocarbon compound such as benzene, toluene, and xylene; an ether compound such as dioxane, tetrahydrofuran, anisole, ethylene glycol dimethyl ether, diethylene glycol dimethyl ether, and diethylene glycol diethyl ether; a nitrile compound such as acetonitrile; a ketone compound such as acetone and 2-butanone; an ester compound such as ethyl acetate and butyl acetate; a sulfone compound such as sulfolane; a sulfoxide compound such as dimethyl sulfoxide and the like. These solvents may be used each alone or as a mixture. In the production process 1, water may be used, if necessary.

The reaction temperature of these two production processes is usually −78 to 100° C., and preferably 0 to 80° C. The reaction time is usually 10 minutes to 24 hours.

Besides the above-described production method, compounds of the present invention can be synthesized by combining two known production processes described below.

[Production Process 3]

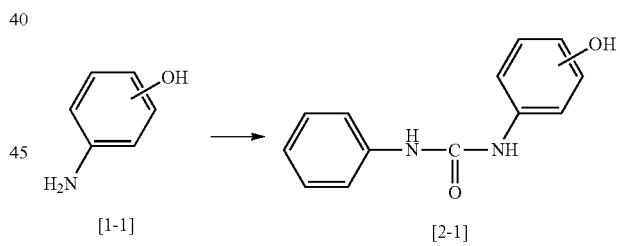

The compound of the above-described general formula [2-1] can be produced by reacting the aminophenol of the formula [1-1] with phenyl isocyanate, in the presence or absence of a base. The amount of phenyl isocyanate used in this reaction is usually 0.1 to 50 molar times, and preferably 0.1 to 5 molar times, with respect to 1 mole of the compound of the general formula [1-1].

Examples of the base which is used, if desired, in this reaction include: an inorganic base such as sodium hydroxide, potassium hydroxide, sodium bicarbonate, sodium carbonate, potassium bicarbonate, potassium carbonate, and cesium carbonate; and an organic base such as triethylamine and diisopropylethylamine. The amounts of these bases used are 0.1 to 50 molar times, and are preferably 1 to 5 molar times, with respect to 1 mole of the compound of the general formula [1-1].

[Production Process 4]

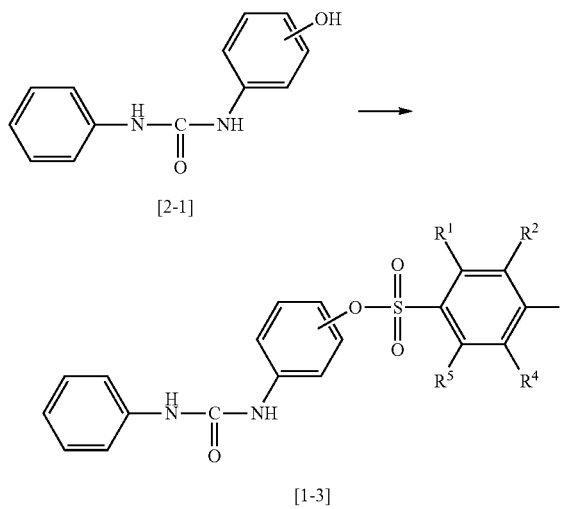

wherein $R^1$ to $R^5$ are as defined above.

A compound of the above-described general formula [1-3] can be produced by reacting the compound of the formula [2-1] with an acid halide represented by [1-5] or an acid anhydride represented by [1-6], in the presence or absence of a base.

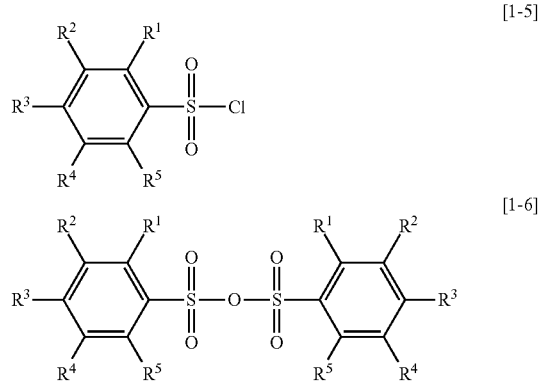

wherein $R^1$ to $R^5$ are as defined above.

The amount of the acid halide or the acid anhydride used in this reaction is 0.1 to 50 molar times, and preferably 1 to 5 molar times, with respect to 1 mole of the compound of the formula [2-1].

Examples of the base which is used, if desired, in this reaction include: an inorganic base such as sodium hydroxide, potassium hydroxide, sodium bicarbonate, sodium carbonate, potassium bicarbonate, potassium carbonate, and cesium carbonate; and an organic base such as triethylamine, pyridine, and diisopropylethylamine. The amount of the base used may be 0.1 to 50 molar times, and may be preferably 1 to 5 molar times, with respect to 1 mole of the compound of the formula [2-1].

The solvent for use in these two production processes are not particularly limited as long as the solvent has no influence on these reactions. Examples of the solvent include: an amide compound such as N,N-dimethylformamide, N,N-dimethylacetamide, and N-methylpyrrolidone; a halogenated hydrocarbon compound such as methylene chloride and chloroform; an aromatic hydrocarbon compound such as benzene, toluene, and xylene; an ether compound such as dioxane, tetrahydrofuran, anisole, ethylene glycol dimethyl ether, diethylene glycol dimethyl ether, and diethylene glycol diethyl ether; a nitrile compound such as acetonitrile; a ketone compound such as acetone and 2-butanone; an ester compound such as ethyl acetate and butyl acetate; a sulfone compound such as sulfolane; a sulfoxide compound such as dimethyl sulfoxide and the like. These solvents may be used each alone or as a mixture. In the production process 4, water may be used, if necessary.

Reaction temperatures of these two production processes are usually −78 to 100° C., and preferably 0 to 80° C. Reaction time may be 10 minutes to 24 hours.

A heat-sensitive recording material according to the present invention comprises a compound represented by the above-described general formula (1) as a color-developing compound. However, the heat-sensitive recording material usually further comprises a color-forming compound which is a color-forming compound, which is typically colorless or light-colored. In addition, if necessary, a heat-sensitive recording material according to the present invention may comprise another color-developing compound, a sensitizer as well as a stabilizer, a binder, a filler, and other additives.

A color-forming compound used in the present invention is not particularly limited and may be ones generally used in a pressure-sensitive recording paper or a heat-sensitive recording paper. In one embodiment of the present invention, examples of the color-forming compound include a fluoran compound, a triarylmethane compound, a spiro compound, a diphenylmethane compound, a thiazine compound, a lactam compound, and a fluorene compound. A fluoran compound is preferable.

Specific examples of the fluoran compound include 3-diethylamino-6-methyl-7-anilinofluoran, 3-dibutylamino-6-methyl-7-anilinofluoran, 3-(N-methyl-N-cyclohexylamino)-6-methyl-7-anilinofluoran, 3-(N-ethyl-N-isopentylamino)-6-methyl-7-anilinofluoran, 3-(N-ethyl-N-isobutylamino)-6-methyl-7-anilinofluoran, 3-[N-ethyl-N-(3-ethoxypropyl)amino]-6-methyl-7-anilinofluoran, 3-(N-ethyl-N-hexylamino)-6-methyl-7-anilinofluoran, 3-dipentylamino-6-methyl-7-anilinofluoran, 3-(N-methyl-N-propylamino)-6-methyl-7-anilinofluoran, 3-(N-ethyl-N-tetrahydrofurylamino)-6-methyl-7-anilinofluoran, 3-diethylamino-6-methyl-7-(p-chloroanilino)fluoran, 3-diethylamino-6-methyl-7-(p-fluoroanilino)fluoran, 3-[N-ethyl-N-(p-tolyl)amino]-6-methyl-7-anilinofluoran, 3-diethylamino-6-methyl-7-(p-toluidino)fluoran, 3-diethylamino-7-(o-chloroanilino)fluoran, 3-dibutylamino-7-(o-chloroanilino)fluoran, 3-diethylamino-7-(o-fluoroanilino)fluoran, 3-dibutylamino-7-(o-fluoroanilino)fluoran, 3-diethylamino-7-(3,4-dichloroanilino)fluoran, 3-pyrrolidino-6-methyl-7-anilinofluoran, 3-diethylamino-6-chloro-7-ethoxyethylaminofluoran, 3-diethylamino-6-chloro-7-anilinofluoran, 3-diethylamino-7-chlorofluoran, 3-diethylamino-7-methylfluoran, 3-diethylamino-7-octylfluoran, 3-[N-ethyl-N-(p-tolyl)amino]-6-methyl-7-phenethylfluoran and the like. 3-Dibutylamino-6-methyl-7-anilinofluoran is preferable.

Specific examples of the triarylmethane compound include 3,3-bis(p-dimethylaminophenyl)-6-dimethylaminophthalide (also called crystal violet lactone or CVL), 3,3-bis(p-dimethylaminophenyl)phthalide, 3-(p-dimethylaminophenyl)-3-(1,2-dimethylaminoindol-3-yl)phthalide, 3-(p-dimethylaminophenyl)-3-(2-methylindol-3-yl)phthalide, 3-(p-dimethylaminophenyl)-3-(2-phenylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazole-3-yl)-5-dimethylaminophthalide, 3,3-(2-phenylindol-3-yl)-5-dimethylaminophthalide, 3-p-dimethylaminophenyl-3-(1-methylpyrrol-2-yl)-6-dimethylaminophthalide and the like.

Specific examples of the spiro compound include 3-methylspirodinaphthopyran, 3-ethylspirodinaphthopyran, 3,3'-dichlorospirodinaphthopyran, 3-benzylspirodinaphthopyran, 3-propylspirobenzopyran, 3-methylnaphtho-(3-methoxybenzo)spiropyran, 1,3,3-trimethyl-6-nitro-8'-methoxyspiro(indoline-2,2'-benzopyran) and the like. Specific examples of the diphenylmethane compound include N-halophenylleuco auramine, 4,4-bis-dimethylaminophenylbenzhydrylbenzyl ether, N-2,4,5-trichlorophenylleuco auramine and the like. Specific examples of the thiazine compound include benzoylleucomethylene blue, p-nitrobenzoylleucomethylene blue and the like. Specific examples of the lactam compound include rhodamine B anilinolactam, rhodamine B-p-chloroanilinolactam and the like. Specific examples of the fluorene compound include 3,6-bis(dimethylamino)fluorenespiro(9,3')-6'-dimethylaminophthalide, 3,6-bis(dimethylamino)fluorenespiro(9,3')-6'-pyrrolidinophthalide, 3-dimethylamino-6-diethylaminofluorenespiro(9,3')-6'-pyrrolidinophthalide and the like. These color-forming compounds may be used each alone or as a mixture.

In one embodiment of the present invention, in combination with a compound of the formula (1), other color-developing compounds may be contained. Such color-developing compounds are not particularly limited, and examples thereof include: a phenolic compound such as α-naphthol, β-naphthol, p-octylphenol, 4-t-octylphenol, p-t-butylphenol, p-phenylphenol, 1,1-bis(p-hydroxyphenyl)propane, 2,2-bis(p-hydroxyphenyl)propane (also called bisphenol A or BPA), 2,2-bis(p-hydroxyphenyl)butane, 1,1-bis(p-hydroxyphenyl)cyclohexane, 4,4'-thiobisphenol, 4,4'-cyclohexylidene diphenol, 2,2'-bis(2,5-dibromo-4-hydroxyphenyl)propane, 4,4'-isopropylidenebis(2-t-butylphenol), 2,2'-methylenebis(4-chlorophenol), 4,4'-dihydroxydiphenylsulfone, 4-hydroxy-4'-methoxydiphenylsulfone, 2,4'-dihydroxydiphenylsulfone, 4-hydroxy-4'-isopropoxydiphenylsulfone, 4-hydroxy-4'-ethoxydiphenylsulfone, 4-hydroxy-4'-butoxydiphenylsulfone, 4-hydroxy-4'-benzyloxydiphenylsulfone, methyl bis(4-hydroxyphenyl)acetate, butyl bis(4-hydroxyphenyl)acetate, benzyl bis(4-hydroxyphenyl) acetate, and 2,4-dihydroxy-2'-methoxybenzanilide; and an aromatic carboxylic acid, a derivative thereof, or a polyvalent metal salt thereof such as benzyl p-hydroxybenzoate, ethyl p-hydroxybenzoate, dibenzyl 4-hydroxyphthalate, dimethyl 4-hydroxyphthalate, ethyl 5-hydroxyisophthalate, 3,5-di-t-butylsalicylic acid, 3,5-di-α-methylbenzylsalicylic acid, zinc 3,5-di-t-butylsalicylate, calcium 3,5-di-t-butylsalicylate and the like.

In one embodiment of the present invention, a sensitizer (a heat-fusible compound) may be contained. Specific examples of the sensitizer (the heat-fusible compound) include waxes such as an animal- or plant-derived wax and a synthetic wax, a higher fatty acid, a higher fatty acid amide, a higher fatty acid anilide, a naphthalene derivative, an aromatic ether, an aromatic carboxylic acid derivative, an aromatic sulfonic acid ester derivative, a carbonic acid or oxalic acid diester derivative, a biphenyl derivative, a terphenyl derivative, a sulfone derivative, an aromatic ketone derivative, an aromatic hydrocarbon compound and the like.

Examples of the wax include Japanese wax, carnauba wax, shellac, paraffin, montan wax, oxidized paraffin, polyethylene wax, oxidized polyethylene and the like. Examples of the higher fatty acid include stearic acid, behenic acid and the like. Examples of the higher fatty acid amide include stearic acid amide, oleic acid amide, N-methylstearic acid amide, erucic acid amide, methylolbehenic acid amide, methylene bis stearic acid amide, ethylene bis stearic acid amide and the like. Examples of the higher fatty acid anilide include stearic acid anilide, linoleic acid anilide and the like. Examples of the naphthalene derivative include 1-benzyloxynaphthalene, 2-benzyloxynaphthalene, phenyl 1-hydroxynaphthoate, 2,6-diisopropylnaphthalene and the like. Examples of the aromatic ether include 1,2-diphenoxyethane, 1,4-diphenoxybutane, 1,2-bis(3-methylphenoxy)ethane, 1,2-bis(4-methoxyphenoxy)ethane, 1,2-bis(3,4-dimethylphenyl)ethane, 1-phenoxy-2-(4-chlorophenoxy)ethane, 1-phenoxy-2-(4-methoxyphenoxy)ethane, 1,2-diphenoxymethylbenzene, diphenylglycol and the like. Examples of the aromatic carboxylic acid derivative include p-hydroxybenzoic acid benzyl ester, p-benzyloxybenzoic acid benzyl ester, terephthalic acid dibenzyl ester and the like. Examples of the aromatic sulfonic acid ester derivative include p-toluenesulfonic acid phenyl ester, phenyl mesitylene sulfonate, 4-methylphenyl mesitylene sulfonate, 4-tolyl mesitylene sulfonate and the like. Examples of the carbonic acid or oxalic acid diester derivative include diphenyl carbonate, oxalic acid dibenzyl ester, oxalic acid di(4-chlorobenzyl) ester, oxalic acid di(4-methylbenzyl) esters and the like. Examples of the biphenyl derivative include p-benzylbiphenyl, p-allyloxybiphenyl and the like. Examples of the terphenyl derivative include m-terphenyl and the like. Examples of the sulfone derivative include p-toluenesulfonamide, benzene sulfone anilide, p-toluene sulfone anilide, 4,4'-diallyloxy diphenyl sulfone, diphenyl sulfone and the like. Examples of the aromatic ketone derivative include 4,4'-dimethylbenzophenone, dibenzoylmethane and the like. Examples of the aromatic hydrocarbon compound include p-acetotoluidine and the like.

In one embodiment of the present invention, a stabilizer may be contained. Specific examples of the stabilizer include: a hindered phenol compound such as 2,2'-methylenebis(4-methyl-6-t-butylphenol), 2,2'-methylenebis(4-ethyl-6-t-butylphenol), 2,2'-ethylidenebis(4,6-di-t-butylphenol), 4,4'-thiobis(2-methyl-6-t-butylphenol), 4,4'-butylidenebis(6-t-butyl-m-cresol), 1-[α-methyl-α-(4'-hydroxyphenyl)ethyl]-4-[α',α'-bis(4'-hydroxyphenyl)ethyl]benzene, 1,1,3-tris(2-methyl-4-hydroxy-5-cyclohexylphenyl)butane, 1,1,3-tris(2-methyl-4-hydroxy-5-t-butylphenyl)butane, tris (2,6-dimethyl-4-t-butyl-3-hydroxybenzyl)isocyanurate, 4,4'-thiobis(3-methylphenol), 4,4'-dihydroxy-3,3',5,5'-tetrabromodiphenyl sulfone, 4,4'-dihydroxy-3,3',5,5'-tetramethyldiphenyl sulfone, 2,2-bis(4-hydroxy-3,5-dibromophenyl) propane, 2,2-bis(4-hydroxy-3,5-dichlorophenyl)propane, and 2,2-bis(4-hydroxy-3,5-dimethylphenyl)propane; an epoxy compound such as 1,4-diglycidyloxy benzene, 4,4'-diglycidyloxy diphenyl sulfone, 4-benzyloxy-4'-(2-methylglycidyloxy)diphenyl sulfone, diglycidyl terephthalate, a cresol novolac type epoxy resin, a phenol novolac type epoxy resin, and a bisphenol A type epoxy resin; N,N'-di-2-naphthyl-p-phenylenediamine, a sodium or polyvalent metal salt of 2,2'-methylenebis(4,6-di-t-butylphenyl)phosphate, bis(4-ethyleneiminocarbonylaminophenyl)methane, a urea urethane compound (such as a color-developing compound UU manufactured by CHEMIPRO KASEI) and a diphenyl sulfone crosslinking type compound represented by the following formula (7) or a mixture thereof or the like.

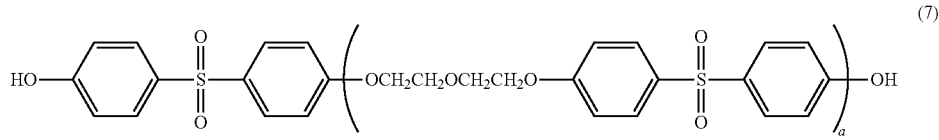

(7)

wherein, a is an integer of 0 to 6.

In one embodiment of the present invention, a binder may be contained. Specific examples of the binder include: a water-soluble polymer such as methyl cellulose, methoxy cellulose, hydroxyethyl cellulose, carboxymethyl cellulose, carboxymethyl cellulose sodium, cellulose, polyvinyl alcohol (PVA), carboxyl group-modified polyvinyl alcohol, sulfonic acid group-modified polyvinyl alcohol, silyl group-modified polyvinyl alcohol, polyvinylpyrrolidone, polyacrylamide, polyacrylic acid, starch and its derivative, casein, gelatin, water-soluble isoprene rubber, an alkali salt of a styrene/maleic anhydride copolymer and an alkali salt of an iso (or diiso) butylene/maleic anhydride copolymer; and a hydrophobic polymer emulsion such as a (meth) acrylate copolymer, a styrene/(meth)acrylate copolymer, polyurethane, polyester-based polyurethane, polyether-based polyurethane, polyvinyl acetate, an ethylene/vinyl acetate copolymer, polyvinyl chloride, a vinyl chloride/vinyl acetate copolymer, polyvinylidene chloride, polystyrene, a styrene/butadiene (SB) copolymer, a carboxylated styrene/butadiene (SB) copolymer, a styrene/butadiene/acrylic acid copolymer, an acrylonitrile/butadiene (NB) copolymer, a carboxylated acrylonitrile/butadiene (NB) copolymer, composite particles of colloidal silica, a (meth)acrylic resin and the like.

In one embodiment of the present invention, a filler may be contained. Specific examples of the filler include calcium carbonate, magnesium carbonate, magnesium oxide, silica, white carbon, talc, clay, alumina, magnesium hydroxide, aluminum hydroxide, aluminum oxide, barium sulfate, a polystyrene resin, a urea-formalin resin and the like.

In embodiments of the present invention, various additives other than those described above may be contained. Examples thereof include: a metal salt of a higher fatty acid such as zinc stearate and calcium stearate, which can be used for preventing the abrasion of thermal heads or preventing sticking; a UV absorber such as a phenol derivative, a benzophenone compound and a benzotriazole compound, which can be used for conferring an antioxidative or anti-aging effect; various surfactants, antifoaming agents and the like.

In the present invention, a composition ratio of each component of the heat-sensitive recording material is not particularly limited. According to one embodiment of the present invention, the heat-sensitive recording material may contain: usually 1 to 50 mass %, and preferably 5 to 30 mass % of a color-forming compound; usually 1 to 70 mass %, and preferably 10 to 50 mass % of a compound represented by the above-described general formula (1); usually 1 to 80 mass % of a sensitizer, usually 0 to 30 mass % of a stabilizer; usually 1 to 90 mass % of a binder; and usually 0 to 80 mass % of a filler; any ratio, for example, usually each 0 to 30 mass %, of each of other additives such as a lubricant, a surfactant, an antifoaming agent and a UV absorber (mass % of each component is the mass ratio in terms of a solid content of each component to the heat-sensitive recording material).

In preferable embodiments of the present invention, a compound represented by the general formula (1) is contained usually in 0.5 to 20 parts by mass, and more preferably in 1 to 5 parts by mass, with respect to 1 part by mass of the color-forming compound, in terms of a solid content.

Next, methods for preparing heat-sensitive recording materials according to the present invention and heat-sensitive recording sheets such as heat-sensitive recording paper using the heat-sensitive recording material are described. According to one embodiment of the present invention, a heat-sensitive recording material can be prepared, for example, by pulverizing and dispersing a color-forming compound and a compound represented by the general formula (1), if necessary, together with a binder or other additives and the like, in a dispersing machine such as a ball mill, an attritor, or a sand mill to prepare dispersions (usually, water is used as a medium for wet pulverization or dispersion) and mixing the dispersions. The obtained heat-sensitive recording material (dispersion) is applied onto a supporting medium such as paper (plain paper, high-quality paper, coated paper or the like can be used), a plastic sheet, or synthetic paper, in such an amount as to usually provide 1 to 20 g/m$^2$ in terms of a dry mass, with a bar coater, a blade coater or the like, and is dried to give a heat-sensitive recording sheet having the heat-sensitive recording material according to the present invention.

If necessary, an intermediate layer may be disposed between a heat-sensitive recording layer and a supporting medium, or an overcoat layer (protective layer) may be disposed on a heat-sensitive recording layer. The intermediate layer or the overcoat layer (protective layer) is disposed, for example, by pulverizing and dispersing the color-developing compound and a color forming compound together with the above-described binder or other additives, if necessary, in the same way as in the preparation of the heat-sensitive recording material coating liquid to prepare a coating liquid for the intermediate layer or a coating liquid for the overcoat layer (protective layer), which is then applied in usually approximately 0.1 to 10 g/m$^2$ in terms of a dry mass and dried to manufacture a sample having the heat-sensitive recording material according to the present invention.

EXAMPLES

Hereinafter, the present invention will be described further specifically with reference to Examples. However, the present invention is not intended to be limited by Examples below by any means. In Examples, "part" means part by mass, and "%" means mass %.

Example 1

Synthesis of Compound No. 2 in Table 1

[Step 1]

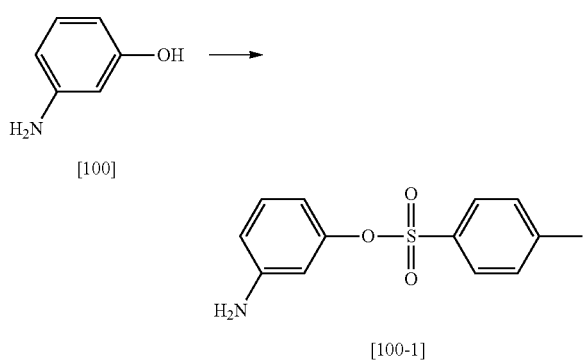

To 52.8 parts of a 25% aqueous sodium hydroxide solution, 30.0 parts of 3-aminophenol [100] (manufactured by Tokyo Chemical Industry Co., Ltd.) were added and the mixture was stirred, and the temperature was raised to 65° C. Then, 52.9 parts of p-toluenesulfonyl chloride (manufactured by Tokyo Chemical Industry Co., Ltd.) were added to the mixture, and the mixture was stirred at the same temperature for 1 hour. After that, deposits were filtered off, and the residue was washed with water and was dried to yield 34.1 parts of the above-described compound [100-1] as a yellow-brown solid.

MS (ESI): [M+H]$^+$: cal.: 264.1, found: 264.1

[Step 2]

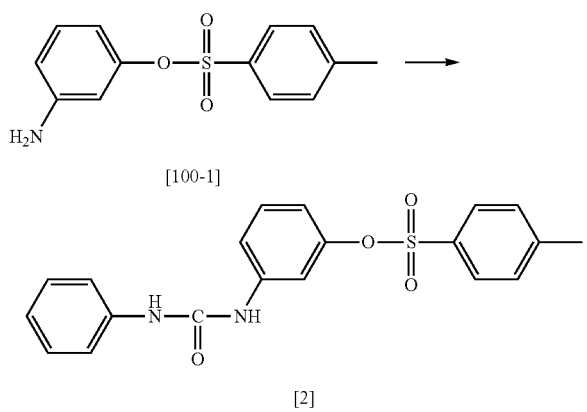

To 25 parts of DMF, 5.0 parts of the above-described compound [100-1] were added and the mixture was stirred. Then, 2.3 parts of phenyl isocyanate (manufactured by Tokyo Chemical Industry Co., Ltd.) were added dropwise to the mixture at room temperature. After the mixture was stirred at the same temperature for 1 hour, the reaction solution was added dropwise into 250 parts of water to deposit crystals. The deposits were washed sequentially with dichloromethane and water, and were dried to yield 4.1 parts of Compound No. 2 in Table 1 as a white solid.

MS(ESI): [M−H]$^-$: cal.: 381.1, found: 381.1

Example 2

Preparation of Heat-Sensitive Recording Material and Heat-Sensitive Recording Paper Containing the Same Compound No. 2 in Table 1 obtained in Example 1 was pulverized and dispersed for 1 hour according to the following composition with a Multi-beads Shocker (Type: PV1001 (S)) manufactured by Yasui Kikai Corporation to prepare Liquid [A].

| Liquid [A]: | Compound No. 2 in Table 1 | 15 parts |
|---|---|---|
| | 25% aqueous PVA solution | 20 parts |
| | Water | 65 parts |

A mixture having the following composition was pulverized and dispersed with a sand grinder such that a median particle diameter was 1 μm, which was measured by a laser diffraction/scattering particle diameter distribution measuring apparatus LA-950 (manufactured by HORIBA, Ltd.), to prepare Dispersion [B] of the color-forming compound.

| Liquid [B]: | 3-dibutylamino-6-methyl-7-anilinofluoran | 35 parts |
|---|---|---|
| | 15% aqueous PVA solution | 40 parts |
| | Water | 25 parts |

Then, each of the liquids obtained as described above and the following agents were mixed according to the following composition to prepare a heat-sensitive recording material coating liquid, which was then applied at 5 g/m$^2$ in terms of a dry mass onto high-quality paper having a basis weight of 50 g/m$^2$, and was dried to prepare a heat-sensitive recording paper having the heat-sensitive recording material according to the present invention.

| Liquid [A] | 40.0 parts |
|---|---|
| Liquid [B] | 8.6 parts |
| 67% aqueous calcium carbonate dispersion | 9.0 parts |
| 48% modified styrene-butadiene copolymer latex | 6.3 parts |
| Water | 36.1 parts |

(Formation of Protective Layer)

Next, a protective layer coating liquid having the following composition was applied at 2 g/m$^2$ in terms of a dry mass onto the above-described heat-sensitive recording paper and was dried to prepare a heat-sensitive recording paper having a protective layer.

| 40% styrene/acrylic acid ester copolymer emulsion | 115 parts |
|---|---|
| 5% aqueous bentonite dispersion | 17 parts |
| 45% aqueous styrene-acryl copolymer emulsion | 44 parts |
| 39% aqueous zinc stearate dispersion | 103 parts |
| 67% aqueous calcium carbonate dispersion | 15 parts |

Example 3

Synthesis of Compound No. 1 in Table 1

[Step 1]

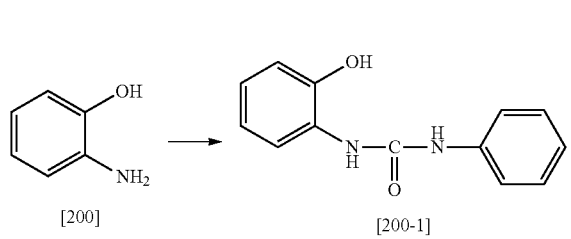 [SMILES: Nc1ccccc1O ; O=C(Nc1ccccc1)Nc1ccccc1O]

To 200 parts of toluene, 20.0 parts of 2-aminophenol [200] (manufactured by Tokyo Chemical Industry Co., Ltd.) were added and the mixture was stirred. Then, 20.7 parts of phenyl isocyanate (manufactured by Tokyo Chemical Industry Co., Ltd.) were added dropwise to the mixture at room temperature. After stirring at the same temperature for 1 hour, deposits were filtered off and the residue was washed with water and was dried to yield 39.5 parts of the above-described compound [200-1] as a yellow solid.

MS(ESI): [M+H]$^+$: cal.: 229.1, found: 229.1

[Step 2]

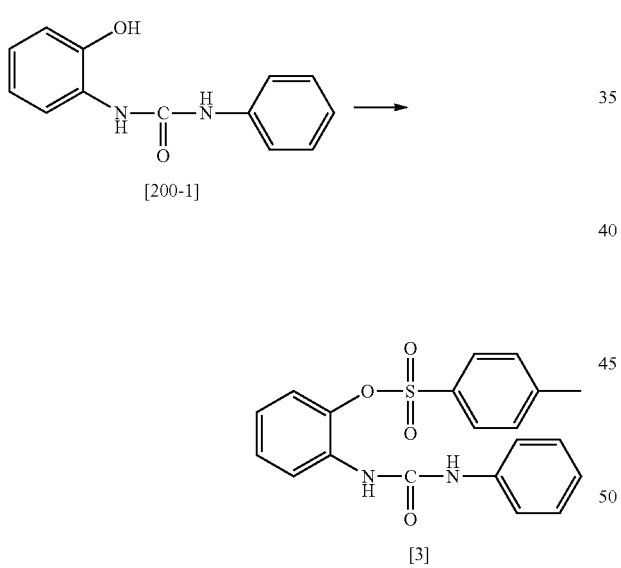

To 100 parts of toluene, 5.0 parts of the above-described compound [200-1] were added and the mixture was stirred. Then, 4.2 parts of p-toluenesulfonyl chloride (manufactured by Tokyo Chemical Industry Co., Ltd.) were added to the mixture at room temperature. At the same temperature, 3.0 parts of pyridine (manufactured by Tokyo Chemical Industry Co., Ltd.) were added dropwise to the mixture, and the mixture was stirred for 1 hour. After that, deposits were filtered off, and the residue was washed with water and was dried to yield 1.9 parts of Compound No. 1 in Table 1 as a white solid.

MS(ESI): [M−H]$^-$: cal.: 381.1, found: 381.1

Example 4

Synthesis of Compound No. 3 in Table 1

[Step 1]

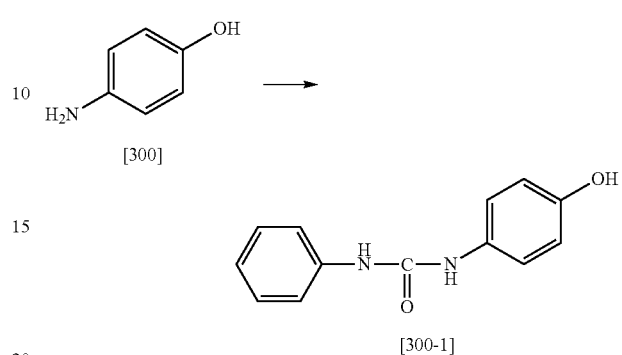

To 100 parts of acetonitrile, 10.0 parts of 4-aminophenol [300] (manufactured by Tokyo Chemical Industry Co., Ltd.) were added and the mixture was stirred. Then, 10.6 parts of phenyl isocyanate (manufactured by Tokyo Chemical Industry Co., Ltd.) were added dropwise to the mixture at room temperature. After stirring at the same temperature for 1 hour, deposits were filtered off, and the residue was washed with water and was dried to yield 19.3 parts of the above-described compound [300-1] as a white solid.

MS(ESI): [M+H]$^+$: cal.: 229.1, found: 229.1

[Step 2]

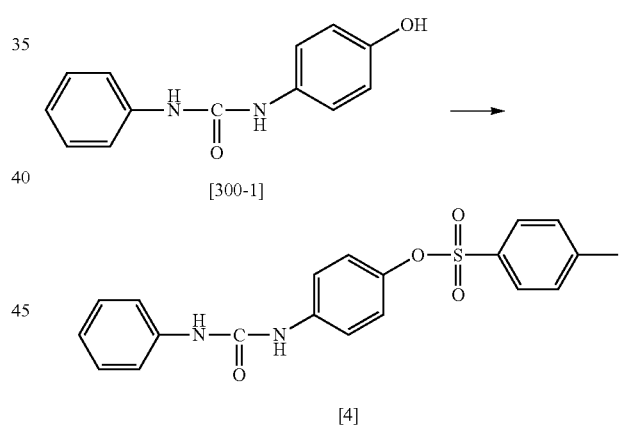

To 500 parts of water, 20.0 parts of the above-described compound [300-1] were added and the mixture was stirred. The mixture was adjusted to pH 8 or higher with a 25% aqueous sodium hydroxide solution, and the temperature was raised to 65° C. Then, 27.8 parts of p-toluenesulfonyl chloride (manufactured by Tokyo Chemical Industry Co., Ltd.) were added to the mixture, and the mixture was stirred at the same temperature for 1 hour. After that, deposits were filtered off, and the residue was washed with water and was dried to yield 29.0 parts of Compound No. 3 in Table 1 as a white solid.

MS(ESI): [M−H]$^-$: cal.: 381.1, found: 381.1

Example 5

A sample having the heat-sensitive recording material according to the present invention was obtained in the same manner as Example 2 except that Compound No. 1 in Table 1 was used instead of Compound No. 2 in Table 1.

Example 6

A heat-sensitive recording paper having the heat-sensitive recording material according to the present invention was obtained in the same manner as Example 2 except that Compound No. 3 in Table 1 was used instead of Compound No. 2 in Table 1.

Comparative Example 1

A mixture having the following composition was pulverized and dispersed with a sand grinder such that a median particle diameter was 1 µm, which was measured by using a laser diffraction/scattering particle diameter distribution measuring apparatus LA-950 (manufactured by HORIBA, Ltd.), to prepare Liquid [C]. For comparison, a heat-sensitive recording paper having a heat-sensitive recording material was prepared in the same manner as Example 2 except that Liquid [C] was used instead of Liquid [A] in the composition of the heat-sensitive recording material coating liquid described in the above-described Example 2 and a heat-sensitive recording material coating liquid was prepared by mixing according to the following composition ratio.

| | |
|---|---|
| Liquid [C]: bisphenol S (manufactured by Tokyo Chemical Industry Co., Ltd.) | 25 parts |
| 25% aqueous PVA solution | 20 parts |
| Water | 55 parts |

Comparative Example 2

A mixture having the following composition was pulverized and dispersed with a sand grinder such that a median particle diameter was 1 µm, which was measured by using a laser diffraction/scattering particle diameter distribution measuring apparatus LA-950 (manufactured by HORIBA, Ltd.), to prepare Liquid [D]. For comparison, a sample having a heat-sensitive recording material was prepared in the same manner as Example 2 except that Liquid [D] was used instead of Liquid [A] in the composition of the heat-sensitive recording material coating liquid described in the above-described Example 2 and a heat-sensitive recording material coating liquid was prepared by mixing according to the following composition ratio.

| | |
|---|---|
| Liquid [D]: Pergafast 201 *[1] | 25 parts |
| 25% aqueous PVA solution | 20 parts |
| Water | 55 parts |

*[1] manufactured by BASF SE, N-(p-toluenesulfonyl)-N'-(3-p-toluenesulfonyloxyphenyl)urea

[Water Resistance Evaluation Test]

The sample having the heat-sensitive recording material obtained in each of Examples 2, 5 and 6 as well as Comparative Examples 1 and 2 put into print at a pulse width of 1.4 msec with a thermal printer (TH-M2/PP) manufactured by Okura Engineering Co., LTD. and then the sample was dipped in water at 25° C. for 24 hours. The Macbeth reflection density of an image in the sample was measured before and after the test with a colorimeter (trade name "SpectroEye") manufactured by Gretag-Macbeth. All of the color measurements were performed using illuminant C as a light source, and ANSI A as a density reference, and under conditions of a viewing angle of 2 degrees. The results are shown in Table 2 below. A higher residual rate means better water resistance. The residual ratio was determined according to the following expression (I):

Residual ratio (%)=(Macbeth reflection density of the image in the sample after the test)/(Macbeth reflection density of the image in the sample before the test)×100  (I)

TABLE 2

| Water resistance in printed part | Example 2 | Example 5 | Example 6 | Comparative Example 1 | Comparative Example 2 |
|---|---|---|---|---|---|
| Residual rate (%) | 100 | 93 | 101 | 84 | 89 |

As is evident from the above-described Table 2, the heat-sensitive recording paper of Example 2 which contains the compound according to the present invention as a color-developing compound exhibited a higher residual ratio than that of Comparative Example 1 which contains bisphenol S, which is the color-developing compound described in Patent Literature 2 and that of Comparative Example 2 which contains Pergafast 201, which is the color-developing compound described in Patent Literature 3. Accordingly, it has been demonstrated that the present invention is superior in images with resistance to water to conventional products.

[Heat Resistance Evaluation Test in Background]

The sample obtained in each of Examples 2, 5 and 6 as well as the one of each of Comparative Examples 1 and 2 was kept at 90° C. for 1 hour with a constant temperature ventilation incubator (trade name, DKN402) manufactured by Yamato Scientific Co., Ltd. The ISO brightness of a background was measured before and after the test with a colorimeter (trade name "SpectroEye") manufactured by Gretag-Macbeth. All of the color measurements were performed using illuminant C as a light source, and ANSI A as a density reference, and under conditions of a viewing angle of 2 degrees. The results are shown in Table 3 below. A smaller amount of change in ISO brightness between before and after the test means better heat resistance of the background.

TABLE 3

| Heat resistance in background part | Example 2 | Example 5 | Example 6 | Comparative Example 1 | Comparative Example 2 |
|---|---|---|---|---|---|
| Before test | 81.1 | 77.9 | 84.0 | 76.7 | 77.0 |
| After test | 76.1 | 75.9 | 80.5 | 64.4 | 62.7 |
| Amount of change | 5.0 | 2.0 | 3.5 | 12.3 | 14.3 |

As is evident from the above-described Table 3, the heat-sensitive recording paper of Example 2 which contains the color-developing compound according to the present invention exhibited a small amount of change in ISO brightness between before and after the heat resistance test. Accordingly, it has been demonstrated that Example 2 is superior in heat resistance of backgrounds to that of Comparative Example 1 which contains bisphenol S, which is the color-developing compound described in Patent Literature 2, and that of Comparative Example 2 which contains Pergafast 201, which is the color-developing compound described in Patent Literature 3.

The invention claimed is:

1. A heat-sensitive recording material comprising a color-forming compound and at least one compound represented by the general formula (1):

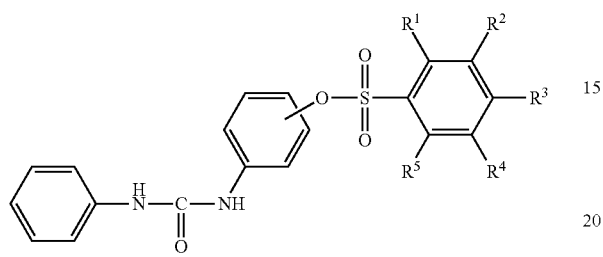

wherein, $R^1$ to $R^5$ each independently represent a hydrogen atom, a halogen atom, a nitro group, an amino group, an alkyl group, an alkoxy group, an aryloxy group, an alkylcarbonyloxy group, an arylcarbonyloxy group, an alkylcarbonylamino group, an arylcarbonylamino group, an alkylsulfonylamino group, an arylsulfonylamino group, a monoalkylamino group, a dialkylamino group, or an arylamino group.

2. The heat-sensitive recording material according to claim 1, wherein the compound of the general formula (1) is a compound represented by the general formula (2):

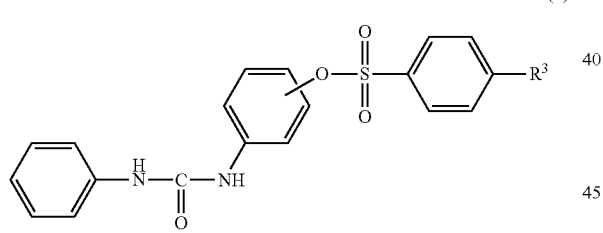

wherein, $R^3$ represents a hydrogen atom, a halogen atom, a nitro group, an amino group, an alkyl group, an alkoxy group, an aryloxy group, an alkylcarbonyloxy group, an arylcarbonyloxy group, an alkylcarbonylamino group, an arylcarbonylamino group, an alkylsulfonylamino group, an arylsulfonylamino group, a monoalkylamino group, a dialkylamino group, or an arylamino group.

3. The heat-sensitive recording material according to claim 2, wherein, $R^3$ is a methyl group.

4. A heat-sensitive recording sheet comprising a support and a layer comprising the heat-sensitive recording material according to claim 1 on said support.

5. A heat-sensitive recording paper comprising a paper support and a layer comprising the heat-sensitive recording material according to claim 1 on said support.

6. A compound represented by the general formula (1):

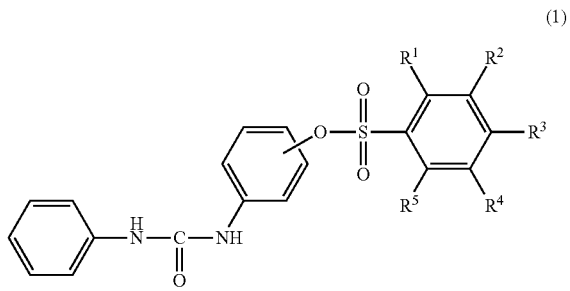

wherein, $R^1$ to $R^5$ each independently represent a hydrogen atom, a halogen atom, a nitro group, an amino group, an alkyl group, an aryloxy group, an alkylcarbonyloxy group, an arylcarbonyloxy group, an alkylcarbonylamino group, an arylcarbonylamino group, an alkylsulfonylamino group, an arylsulfonylamino group, a monoalkylamino group, a dialkylamino group, or an arylamino group.

7. The compound according to claim 6, wherein the compound of the general formula (1) is a compound represented by the general formula (2):

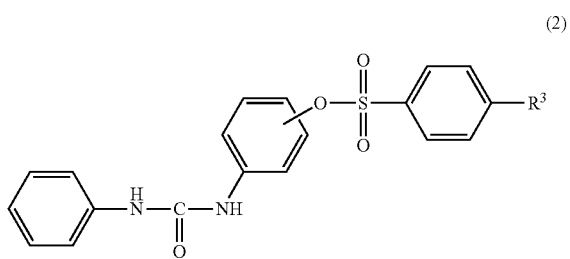

wherein, $R^3$ represents a hydrogen atom, a halogen atom, a nitro group, an amino group, an alkyl group, an aryloxy group, an alkylcarbonyloxy group, an arylcarbonyloxy group, an alkylcarbonylamino group, an arylcarbonylamino group, an alkylsulfonylamino group, an arylsulfonylamino group, a monoalkylamino group, a dialkylamino group, or an arylamino group.

8. A compound represented by any one of the formulae (3) to (5):

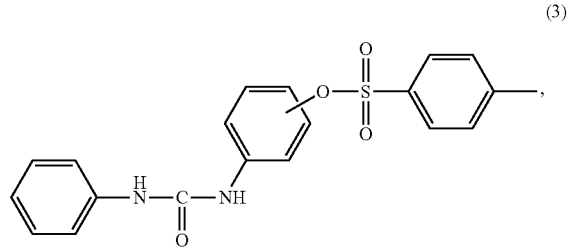

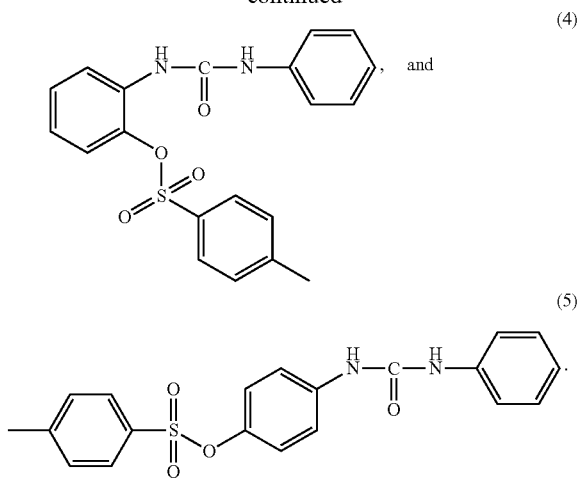

9. A heat-sensitive recording sheet comprising a support and a layer comprising the heat-sensitive recording material according to claim 2 on said support.

10. A heat-sensitive recording sheet comprising a support and a layer comprising the heat-sensitive recording material according to claim 3 on said support.

11. A heat-sensitive recording paper comprising a paper support and a layer comprising the heat-sensitive recording material according to claim 2 on said support.

12. A heat-sensitive recording paper comprising a paper support and a layer comprising the heat-sensitive recording material according to claim 3 on said support.

* * * * *